United States Patent [19]

Pannwitz

[11] Patent Number: 4,783,316
[45] Date of Patent: Nov. 8, 1988

[54] COLORIMETRIC GAS DOSIMETER

[75] Inventor: Karl-Heinz Pannwitz, Lübeck, Fed. Rep. of Germany

[73] Assignee: Drägerwerk AG, Fed. Rep. of Germany

[21] Appl. No.: 913,750

[22] Filed: Sep. 30, 1986

[30] Foreign Application Priority Data

Oct. 1, 1985 [DE] Fed. Rep. of Germany ....... 3534934

[51] Int. Cl.$^4$ ............................................. G01N 31/22
[52] U.S. Cl. ......................................... 422/58; 422/86; 422/88; 436/902
[58] Field of Search ............................ 422/58, 83, 86; 436/902

[56] References Cited

U.S. PATENT DOCUMENTS

| 3,033,655 | 5/1962 | Grosskopf | 422/86 |
| 3,100,692 | 8/1963 | Wächter | 422/86 |
| 3,388,975 | 6/1968 | Wallace | 422/86 X |
| 4,071,319 | 1/1978 | Nugent | 422/86 X |
| 4,267,023 | 5/1981 | Frant et al. | 436/902 X |
| 4,348,358 | 9/1982 | McKee et al. | 422/58 X |
| 4,528,160 | 7/1985 | Eckstein et al. | 422/86 |
| 4,539,181 | 9/1985 | Westrup | 422/59 X |
| 4,554,133 | 11/1985 | Leichnitz | 422/56 X |
| 4,680,165 | 7/1987 | Vo-Dinh | 422/88 |

Primary Examiner—Barry S. Richman
Assistant Examiner—Jill Johnston
Attorney, Agent, or Firm—McGlew and Tuttle

[57] ABSTRACT

A colorimetric gas dosimeter, which contains a granular indicator substance in a closed, transparent, hollow unit that can be opened on one side, is provided in such a way that the diffusion cross section for the hazardous substance molecules is independent of the degree of discoloration of the indicator substance and the detection sensitivity is thereby increased. This is achieved by sub-dividing the hollow unit into several chambers extending along its longitudinal axis, at least one of which is filled with the granular indicator, and is located adjacent to an indicator free chamber and is separated from this by a separating wall permeable to gas.

11 Claims, 1 Drawing Sheet

U.S. Patent    Nov. 8, 1988    4,783,316
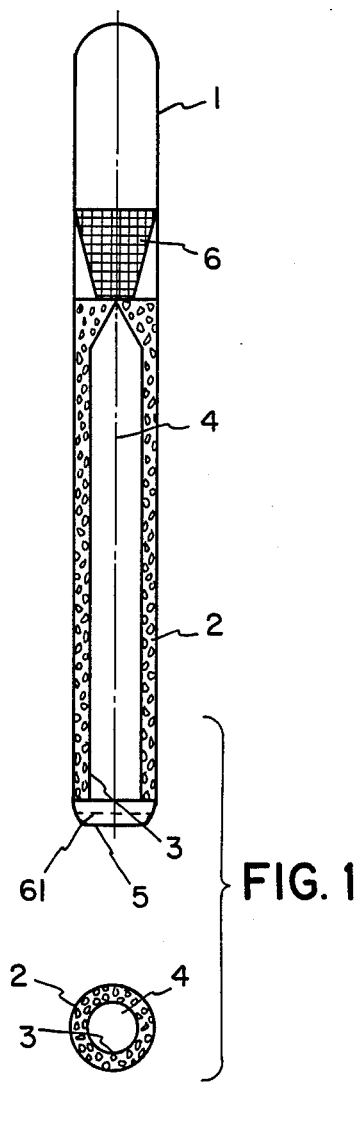
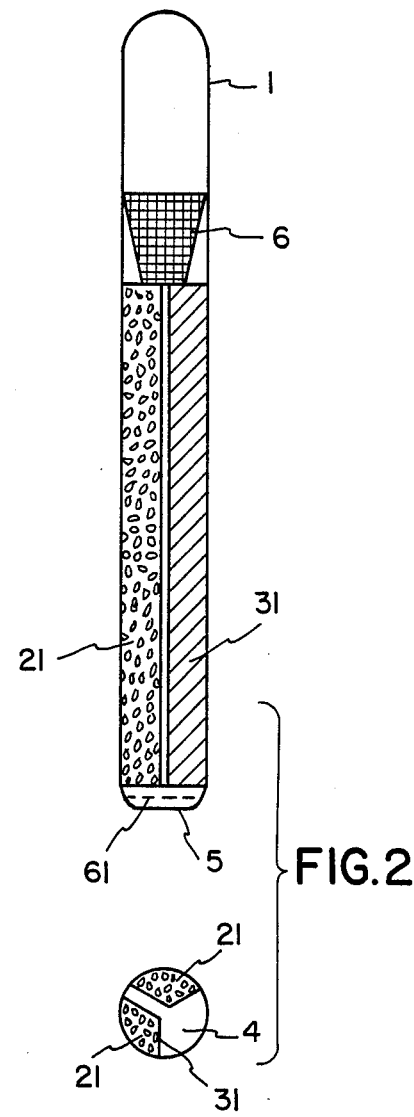

COLORIMETRIC GAS DOSIMETER

FIELD AND BACKGROUND OF THE INVENTION

This invention relates in general to devices for testing gases and in particular to a new and useful colorimetric gas dosimeter comprising longitudinally elongated transparent element subdivided into a plurality of chambers extending along its longitudinal axis.

The invention concerns a colorimetric gas dosimeter, which contains a granular indicator substance in a closed, transparent, hollow unit that can be opened on one side.

A gas dosimeter of this type is described in German OS No. 14 98 909. The known dosimeter is a glass tube filled with a granular indicator material, which can be opened on one side to allow gas to diffuse from there through the interior of the glass tube and that the hazardous substance to be detected causes a discoloration in the indicator material. The zone of discoloration extends along the dosimeter tube with the continued diffusion of the hazardous substance into the indicator material. The indicating sensitivity of the known gas dosimeters depends mainly on the ratio of the effective diffusion cross section to the surface of the cross section of the indicator layer. Small amounts of gaseous hazardous substances to be detected result in a weaker discoloration of the still unchanged color of the indicator as the zone of discoloration progresses. The reason for this is found in the fact that the hazardous substance molecules, permeating the indicator at the opening must traverse an ever extending zone of discoloration before they reach the interphase of the indicator between the zone of discoloration and the unchanged zone, to enter into a chemical reaction of discoloration with the indicator there. During the traversing of the indicator zone already changed in color, the molecules of hazardous substance newly diffusing into the gas dosimeter are hindered in their diffusion to the indicator layer still unchanged in color by the packing of the spent granular indicator material. The diffusion cross section for the molecules of hazardous substance newly entering the opening is thereby considerably decreased. Consequently, the known gas dosimeters are not suitable with low concentrations of hazardous substances for an early detection of hazardous doses since the amount of indicator offered in the first layers attracts the diffusion molecules of hazardous substances by chemisorption within an insignificant length, in comparison with the total length of the indicator, making the resulting zone of discoloraion inaccessible for a quantitative evaluation.

SUMMARY OF THE INVENTION

Thus the present invention provides a colorimetric gas dosimeter in such a way that the diffusion cross section for the molecules of hazardous substance to be detected is independent of the degree of discoloration in the indicator substance and the detection sensitivity is thus increased.

In accordance with the invention a hollow unit is divided into several chambers extending along its longitudinal axis, at least one of which is filled with the granular indicator and adjoins an indicator free chamber and is separated from this by a dividing wall permeable to gas.

A gas dosimeter of this type offers the advantage that the diffusion path determining the indicating speed is now spatially separated from the indicator substance and its zone of discoloration. When the opened gas dosimeter is exposed to the atmosphere containing the hazardous substance, the hazardous substance diffuses into the indicator free chamber and enters from there through the separating wall permeable to gas into the indicator. At the beginning of the exposure, the indicator substance at the start of the diffusion path is discolored since the adsorption of the molecules of hazardous substance to be detected on the granular indicator substance occurs from the beginning due to the prevailing concentration gradient of the molecules of hazardous substance. With continuing discoloration, the adsorption of the molecules of hazardous substance on the unchanged indicator substance will result in an equally clearly separated zone of discoloration, as is the case at the beginning of exposure. The concentration gradient between the atmosphere containing the hazardous substance and the unchanged indicator material results in a diffusion of the molecules of hazardous substance within the indicator free chamber that takes place unhindered by the granular, already discolored indicator substance. A smaller amount of indicator substance is provided for a given amount of molecules of hazardous substance than with the known testing tubes. Thus a considerable increase in the effective cross section is obtained, which results in an increased detection sensitivity.

The separating wall permeable to gas can comprise, to advantage, a wire cloth or paper fiber tissue or other suitable plastics cloth that are inert with respect to the hazardous substance to be detected and the reagents used and which retain the granular indicator in its chamber. Respective polyethylene plastic cloths or foils as well as polyethylene filter papers or fiber-glass cloth can be used similarly.

The hollow unit preferably comprises a glass tube in which the separating wall is located concentrically and spatially separated. The indicator free chamber is located centrally in the hollow unit or in the ring chamber bound by separating wall and hollow unit. The zone of discoloration of the indicator can then be read on any side of the gas dosimeter. But various other geometric arrangements of indicator free and indicator filled chamber are conceivable, depending on requirements.

An especially advantageous arrangement comprises several chambers filled with indicator substances suitable for the detection of different hazardous substances. Since each of the chambers is separated by a separating wall from an indicator free chamber, the molecules of different hazardous substances possess a diffsion cross section that is not influenced by the indicator substances to be allocated to them.

An object of the invention is to provide a device for testing gases which includes a closed transparent hollow longitudinally elongated unit that can be opened at one end and which is subdivided to a plurality of chambers extending along its longitudinal axis with at least one of the chambers being filled with a granular indicator an adjacent one being free of the granular material, the chambers being separated by a gas permeable wall.

A further object of the invention is provide a device for testing gas which is simple in design, rugged in construction and economical to manufacture.

The various features of novelty which characterize the invention are pointed out with particularity in the claims annexed to and forming a part of this disclosure.

For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 1 is a sectional view of a gas dosimeter constructed in accordance with the invention; and FIG. 2 is a sectional view of another embodiment of the invention of a gas dosimeter with several indicator filled chambers.

DESCRIPTION OF THE PREFERRED EMBODIMENT

Referring to the drawings in particular the invention embodied therein in FIG. 1 comprises a gas testing device in the form of a hollow tube or unit 1 which is transparent and has a closed upper end and an opposite openable end 5. The gas permeable separating wall structure 3 extends along the axis of the tube 1 and defines a plurality of separate axially extending chambers. At least one of the chambers, chamber 2 contains a granular color changing gas indicating substance in at least one of the other of said chambers, chamber 4 which is axially contiguous to the first one of the chambers, 2 and is free of indicating substance. Means are provided for holding the substance in the arranged axially or longitudinally extending positions including holding element 6 arranged at one end of the flat end portion of the permeable wall 3 and a holder 61 arranged at the opposite end.

The hollow unit in the form of a glass tube 1 has in its interior a chamber 2 that has an annular cross section and is filled with the porous indicator substance and is adjacent to the wall of glass tube 1. Chamber 2 is separated from the inner, indicator-free chamber 4 by a separating wall 3, which is permeable to gas. The access for the gas to be determined to the indicator free chamber is through the only opening 5 of glass tube 1. Both chambers 2 and 4 are fixed in their positions by a holding element 6.

The glass tube 1 shown in FIG. 2 has two adjacent chambers 21, each filled with a different indicator substance. A separating wall 31 separates these two chambers from one another and from the indicator free chamber 4, through which the hazardous substance molecules diffuse via opening 5 into the respective indicator substance and the indicator free chamber 4 are fixed in their positions by holding element 6 and by the holding element 6 permeable to gas.

While a specific embodiment of the invention has been shown and described in detail to illustrate the application of the principles of the invention, it will be understood that the invention may be embodied otherwise without departing from such principles.

What is claimed is:

1. A colorimetric gas dosimeter comprising a closed transparent hollow longitudinally and elongated unit having frangible means at an end thereof for detaching said end, a gas permeable wall structure subdividing said hollow unit into a plurality of chambers extending along its longitudinal axis, at least one of said chambers being filled with a granular indicator and at least one adjacent chamber being free of filling material, said chamber which is filled with indicator material defining a zone of changeable color of said indicator material extending along said tube and said filling material free chamber defining a gas diffusion chamber extending along said tube.

2. A colorimetric gas dosimeter according to claim 1, wherein said gas permeable wall comprises a wire cloth.

3. A colorimetric gas dosimeter according to claim 1, wherein said hollow unit comprises a glass tube and is herein said gas permeable wall is arranged concentrically at a spaced location from an outer wall of said hollow unit.

4. A colorimetric gas dosimeter according to claim 1, wherein said hollow unit contains a plurality of chambers with said plurality being filled with different indicator substances suitable for detection of different hazardous substances.

5. A gas testing device comprising a transparent tube having a closed end and an opposite openable end frangible means at said openable end for detaching said openable end, a gas permeable separating wall structure extending along the axis of said tube and defining a plurality of separate axially extending chambers, at least one of said chambers containing a granular color changing gas indicator substance and at least one other of said chambers which is axially contiguous to at least one of said chambers being free of filling substance, at least one of said chambers being filled with indicator to define a zone of changeable color of said indicator material extending along said tube and at least one of said chambers which is free of filling substance defining a gas diffusion chamber extending along said tube.

6. A gas testing device according to claim 5, wherein said filling substance free chamber comprises a cylindrical chamber extending centrally within said hollow unit with the indicator chamber extending around the centrally located chamber.

7. A gas testing device according to claim 5, including a holding element arranged at each end of the plurality of chambers holding said gas permeable wall in a position to contain the granular material of said plurality of chambers, said filling substance free chamber having a tapered end toward the closed end of said hollow unit.

8. A gas testing device according to claim 7, wherein said gas permeable wall extends radially on one side of said indicator chamber and includes space permeable portions separating an additional chamber filled with additional granular material indicator substance.

9. A gas testing device according to claim 8, wherein said filling substance free chamber includes a portion extending radially between said indicator chamber and said additional chamber.

10. A colorimetric gas dosimeter comprising a closed transparent hollow longitudinally elongated unit having frangible means at an end thereof for detaching said end, a long gas permeable wall structure extending along the interior of said unit and subdividing said hollow unit into a plurality of contiguous chambers extending along its longitudinal axis, at least one of said chambers being filled with a granular indicator and at least one adjacent chamber being free of filling material, said at least one chamber which is filled with indicator material defining a zone of exteriorly visible changeable color of said indicator material extending along said tube and said filling material free chamber defining an exteriorly visible gas diffusion chamber extending along said tube.

11. A colorimetric dosimeter according to claim 10, wherein said wall structure includes two radially extending wall portions which are spaced apart and which separate two chambers which are filled with granular indicator of different characteristic, said wall structure also including two wall portions which extend at an obtuse angle to each other and which borders the other portions of said two chambers.

* * * * *